United States Patent [19]
Baker et al.

[11] Patent Number: 4,656,143
[45] Date of Patent: Apr. 7, 1987

[54] HETEROGENEOUS BINDING ASSAY

[76] Inventors: Terence S. Baker, 70, Welley Road, Wraysbury, Staines, Middlessex TW19 5EP; Stephen R. Abbott, 28, Kingfisher Drive, Woodley, Reading, RG5 3LG; John G. Simpson, 1, Woodhurst Lane, Emmbrook, Wokingham, Berkshire; John F. Wright, 9, Selcourt Close, Woodley, Reading, RG5 3AS; Michael J. Powell, 89 Aysgarth Park, Holyport, Maidenhead, Berkshire, SL6 2HQ, all of England

[21] Appl. No.: 611,351

[22] Filed: Mar. 15, 1984

[30] Foreign Application Priority Data

Mar. 15, 1983 [GB] United Kingdom ................ 8307156

[51] Int. Cl.$^4$ ................ G01N 33/552; G01N 33/546; G01N 33/537
[52] U.S. Cl. .................................... 436/527; 436/529; 436/531; 436/533; 436/534; 436/538; 436/824; 436/826
[58] Field of Search ............... 436/523, 528, 531, 533, 436/534, 538, 824, 826, 529, 527

[56] References Cited

U.S. PATENT DOCUMENTS

| Re. 29,474 | 11/1977 | Axen et al. | 436/528 |
| 3,995,019 | 11/1976 | Jerome | 436/500 |
| 4,014,651 | 3/1977 | Bettinger et al. | 436/500 |
| 4,088,746 | 5/1978 | Blakemore et al. | 436/500 |
| 4,259,207 | 3/1981 | Fruitstone et al. | 436/826 |
| 4,416,813 | 11/1983 | Ikeda et al. | 436/528 |

FOREIGN PATENT DOCUMENTS

| 0005271 | 3/1979 | European Pat. Off. | 436/528 |
| 1340180 | 12/1973 | United Kingdom | 436/534 |
| 1540098 | 2/1979 | United Kingdom | 436/534 |
| 2019562 | 4/1979 | United Kingdom | 534/ |
| 1564987 | 4/1980 | United Kingdom | 436/534 |

OTHER PUBLICATIONS

Mamelok et al, Chemical Abstracts, vol. 95 (1981) Abstract #145919c.
Johansson et al, Chemical Abstracts, vol. 87 (1977) Abstract #103557n.

Primary Examiner—Christine M. Nucker
Attorney, Agent, or Firm—Cushman, Darby & Cushman

[57] ABSTRACT

A heterogeneous binding assay in which a liquid component and a granular particulate solid phase are incubated together for a predetermined period of time. To prevent unwanted unit gravity sedimentation of the granular particulate solid phase during incubation the density of the liquid component is controlled such that it is substantially equal to the density of the granular particulate solid phase, thus preventing sedimentation. The density may be controlled by adding a density modifying medium such as a colloidal suspension of silica particles coated with polyvinylpyrrolidine. After incubation, the density of the liquid component may be reduced allowing unit gravity sedimentation and hence separation of the solid phase from the liquid component. The assay is particularly applicable to immunoassay (for example radioimmunoassay and immunoradiometric assay). Immunoradiometric assays for human growth hormone, thyroid stimulating hormone and alphafetoprotein are described.

4 Claims, 4 Drawing Figures

HETEROGENEOUS BINDING ASSAY

This invention relates to a heterogeneous binding assay in which a liquid component and a granular particulate solid phase are incubated together for a predetermined period of time. The invention relates especially to an immunometric assay and also relates to kits for performing the heterogeneous binding assay of the invention.

The basis of a binding assay is a binding interaction between a molecule of analyte in a sample and a specific binding partner. An assay result is obtained by incubating the sample containing analyte with the specific binding partner for a predetermined period and determining the amount of specific binding partner which has become bound to analyte. In a heterogeneous binding assay the determination is facilitated by physically separating the components of the assay. This is achieved by attaching a component of the assay to a solid phase which may be physically removed from the liquid component of the assay, following incubation. A large number of variants of heterogeneous binding assays are known, the most common being assays for antigenic analytes which involve the use of antibody as a specific binding partner. Examples of such assays are immunoassays such as radioimmunoassay (RIA) and immunometric assays such as immunoradiometric assay (IRMA). In RIA a radiolabelled analogue of an antigenic analyte competes in solution during incubation with the antigenic analyte for binding to antibody attached to a solid phase. After a suitable predetermined incubation period the solid phase is removed from the solution, is washed, and the amount of radiolabel associated with the solid phase is measured. This gives an inverse measure of the amount of antigenic analyte in the sample. In IRMA a similar protocol is followed except that a labelled antibody is used to provide a detectable signal. In a particular type of IRMA, commonly known as a "sandwich assay", a solid phase is provided with an antibody capable of binding to a determinant of the antigenic analyte. A second, labelled, antibody to another determinant of the antigenic analyte is provided in a liquid component. The solid phase and the liquid component are incubated together with the sample suspected to contain analyte. Any analyte present becomes attached to the solid phase and labelled antibody becomes attached to the analyte. After incubation the solid phase is separated from the liquid component and the amount of label associated with the solid phase is measured, this giving a direct indication of the amount of analyte present.

A number of different types of solid phase are available for use in heterogeneous binding assays. These range from "single particle" systems such as coated tubes and beads, to finely divided particulate materials such as microcrystalline cellulose or finely divided silica. The choice of a solid phase is governed by a number of factors, including capacity for the binding agent (connected with total surface area) and the convenience of use of the solid phase. For example, finely divided particulate materials have the advantage that they are easy to dispense but the disadvantage that centrifugation is necessary to separate the solid phase from the liquid component of the assay reagents. "Single particle" systems do not require centrifugation but suffer from variability and insufficient capacity for binding reagent.

An intermediate-sized solid phase provides a compromise between the two extreme solid phase systems referred to above. Such intermediate-sized solid phases are referred to as "granular particulate solid phases" herein and in general have a high binding reagent capacity and are of sufficient size and density to allow separation under gravity (an acceleration of 1 g). Such a separation is commonly referred to as unit gravity sedimentation. (Wright, J. F. and Hunter, W. M. Immunoassays for Clinical Chemistry, pp 170–177, Churchill-Livingstone 1983). A solid phase of this type does not require centrifugation for separation and has a sufficient binding reagent capacity to allow satisfactory assays to be performed. By removing the need for centrifugation to separate the solid phase from the liquid component of the assay reagents after incubation, the assay protocol is greatly simplified. In particular a density separation technique such as is described in British patent specification No.1566098 may be used in conjunction with a granular particulate solid phase to provide a simple and inexpensive assay.

A remaining disadvantage of such an assay is however that the granular particulate solid phase settles downwardly in the liquid component of the assay during incubation. This significantly impairs the interaction of the binding species, reducing both the sensitivity and the accuracy of the assay. In using such an assay it is therefore necessary continuously to agitate the mixture of the granular particulate solid phase and the liquid component of the assay reagents to ensure that the solid phase is kept in free suspension. In addition where the solid phase is stored in a container as a suspension in a liquid it is necessary to ensure that all the solid phase is in suspension before use to avoid inaccurate dispensing.

The present invention provides a method for performing heterogeneous binding assay using a granular particulate solid phase, which does not require agitation during incubation.

According to the present invention there is provided a heterogeneous binding assay in which a liquid component and a granular particulate solid phase are incubated together for a predetermined period of time, characterised in that the density of the liquid component is maintained substantially equal to the density of the granular particulate solid phase at least during the predetermined period of time.

In this way settling of the granular particulate solid phase under the influence of gravity is prevented or at least substantially reduced. The term "substantially equal" as used herein means that the density of the liquid component is maintained equal to the density of the granular particulate solid phase with sufficient accuracy to prevent substantial floating or sedimentation of the granular particulate solid phase during incubation. This removes the need for agitation of the assay components during incubation with the resulting advantage that the assay protocol is simplified and the need for an agitator is removed.

The granular particulate solid phase comprises particles of a material, of a suitable size and density to allow separation under gravity (unit gravity sedimentation) from a normal incubation mixture in a reasonable time. The granular particulate solid phase suitably separates under gravity from a normal incubation mixture in from 5 to 30 minutes, most suitably from 5 to 15 minutes (for example in about 20 minutes). Suitable granular particulate solid phases include porous particles such as dextran, agarose and acrylamide polymers and copolymers or non-porous particles such as latex particles. Examples of suitable granular particulate solid phase particles are Sepharose, Sephadex and Sephacryl. Sephacryl particles are particularly preferred, especially Sephacryl S-300. Sephacryl is a rigid gel prepared by covalently cross-linking allyl dextran with N, N'-methylene bisacrylamide. Particles of Sephacryl S-300 have diameters in the range 40–105 μm.

Preferably the density of the liquid component is maintained substantially equal to the density of the granular particulate solid phase by the addition of a density modifying medium having a density greater than the density of the granular particulate solid phase.

Suitable density modifying media include non-toxic high molecular weight materials which do not adversely affect the components of the assay system and which suitably provide a relatively low viscosity solution. The density modifying medium may comprise a solution of a sugar (for example sucrose), another carbohydrate (for example, dextran or Ficoll—a high molecular weight hydrophilic polymer of sucrose), or another polymer (for example, polyvinylpyrrolidine). Where the granular particulate solid phase is porous however such density modifying media may be absorbed into the granular particulate solid phase and affect its density. In such cases an insoluble density modifying medium such as a colloid is suitable. Preferably the density modifying medium is a colloidal suspension of silica particles coated with polyvinylpyrrolidine. Such a suspension is commercially available and is known as Percoll.

Preferably the granular particulate solid phase comprises an allyl dextran cross-linked with N,N'-methylene bisacrylamide and the density modifying medium comprises a colloidal suspension of silica particles coated with polyvinylpyrrolidine.

In a preferred assay using Sephacryl S-300 as a granular particulate solid phase it has been found that the incorporation of a coloidal suspension of Percoll into the liquid component of the assay at about 40% (v/v) raises the density of the liquid component sufficiently to maintain the granular particulate solid phase in suspension for about 4 hours. This period is ample for most assays.

Following incubation for a predetermined period of time it is necessary to separate the granular particulate solid phase from the liquid component.

Preferably the density of the liquid component is reduced upon expiry of the predetermined period of time to allow the granular particulate solid phase to separate under the influence of gravity by diluting the liquid component and medium mixture with a liquid of lower density than the liquid and medium mixture. Suitably a diluent such as water or a buffer is added to the liquid component and medium mixture, decreasing the density of the mixture and allowing the granular particulate solid phase to separate under the influence of gravity. Separation of the remainder of the liquid component and medium mixture from the solid phase may be completed by any suitable method, including centrifugation. Preferably however the separation method disclosed in British patent specification No.1566098 is used to separate the granular particulate solid phase from the incubation mixture. For example, after incubation diluent may be added to the incubation mixture to decrease the density of the mixture. A second liquid, suitably a 10% sucrose solution is layered below the incubation mixture and the granular particulate solid phase is separated under the influence of gravity into the second liquid. The use of such a separation technique advantageously obviates the need for centrifugation. In its preferred form therefore the invention provides a method for performing heterogeneous binding assay which does not require agitation during incubation and further does not require centrifugation to separate the solid phase from the liquid component.

The assay of the invention may be an immunoassay such as an RIA or, preferably, an immunometric assay, for example an IRMA. The label used in the assay may be a radioactive label or any label known in the art, for example fluorophores, chromophores, enzymes, chemiluminescent groups etc. The assay may be used for the determination of a wide range of analytes in solution. Such analytes may be of clinical and/or diagnostic importance and include; hormones, (for example, thyroid stimulating hormone (TSH), human growth hormone (hGH) follicle stimulating hormone (FSH) and luteinising hormone (LH)), steroids and their metabolites (for example, oestrogens and progestagens), diagnostic proteins (for example, alphafoetoprotein (AFP)) and antigens (for example, chlamydia and herpes virus antigens).

The incubation time for a heterogeneous binding assay is often a number of hours and represents a significant disadvantage in the performance of such assays.

The essence of a heterogeneous binding assay is in the provision of a binding partner attached to a solid phase such that components of the assay may be removed from solution by association with the binding partner attached to the solid phase, which may be subsequently removed from solution. This requires an association between a solid phase and a liquid phase which as such is kinetically unfavourable, leading to a need for lengthy incubation.

Preferably there is provided a heterogeneous binding assay involving
a solution containing components of the assay including a binding partner to which biotin is covalently attached and
a granular particulate solid phase to which avidin is covalently attached,
the assay comprising the steps of;
incubating the solution components of the assay in the absence of the granular particulate solid phase,
placing the incubated solution component in contact with the granular particulate solid phase thereby allowing association of avidin and biotin, and
separating the granular particulate solid phase from the solution components.

An assay of this preferred type allows incubation of the active assay components in solution to form bound species and the rapid immobilisation of the species onto the granular particulate solid phase. The preferred assay is particularly useful in the performance of immunometric assay of the sandwich type. In such an assay a labelled antibody, the sample suspected to contain analyte and antibody to which is attached biotin, may be incubated in solution. A ternary immunocomplex will be formed with any analyte in solution. The immunocomplex may be attached to a granular particulate solid phase to which is attached avidin, in a subsequent step, by means of the biotin/avidin interaction. The amount of label associated with the granular particulate solid phase may then be measured. The assay method significantly reduces the incubation period necessary in a binding assay. This reduction in incubation time speeds up the overall time necessary to perform a given assay and in the case of assay involving unit gravity sedimentation reduces the possibility of unwanted sedimentation during incubation.

In another aspect of the invention we provide a kit for performing a heterogeneous binding assay of the invention comprising one or more containers of assay reagents charactersied in that a density modifying medium is provided either in a separate container or in one or more of the containers of assay reagents.

Preferably we provide a kit for performing an immunometric assay for an antigenic analyte in a sample, the kit comprising the following reagents;

a labelled antibody to the analyte, an antibody to the analyte attached to a granular particulate solid phase, and a density-modifying medium, the reagents being contained either separately or in any combination in one or more containers.

Preferably the kit comprises a first container containing the antibody to the analyte attached to the granular particulate solid phase, in suspension in a liquid containing density-modifying medium such that the density of the liquid is substantially equal to the density of the granular particulate solid phase, a second container containing a labelled antibody to analyte and a quantity of density-modifying medium, such that when the reagents in the first and second containers are mixed with the sample, the density of the liquid component is substantially equal to the density of the granular particulate solid phase. The inclusion of density-modifying medium in the first container has the advantage that the granular particulate solid phase is held in a uniform suspension thus facilitating accurate dispensing of the reagent.

Preferably the kit comprises the following reagents;

a labelled antibody to the analyte, an antibody to the analyte to which biotin is covalently attached, a granular particulate solid phase to which avidin is convalently attached, and a density-modifying medium, the reagents being contained either separately or in any combination in one or more containers.

Embodiments of the invention are now described with reference to the following Examples. The Examples refer to the accompanying drawings in which.

EXAMPLE 1

Figure 1:
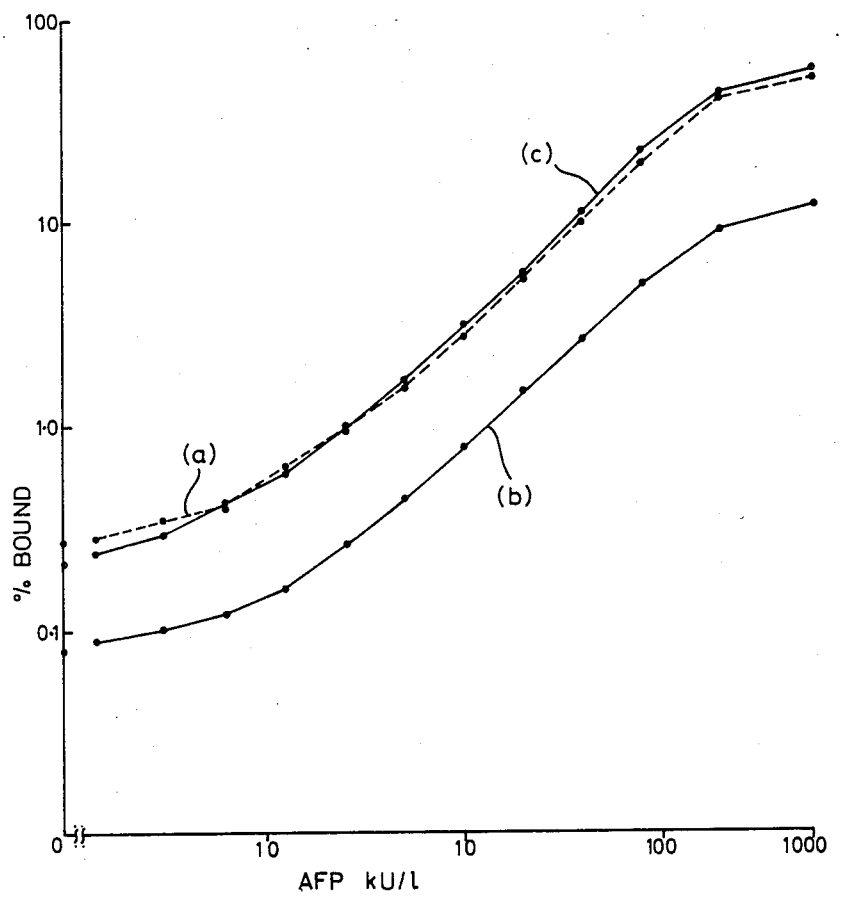
FIG. 1 shows standard curves for an alphafetoprotein immunoradiometric assay (curve (c) shows the result of an assay performed in accordance with the present invention; curves (a) and (b) show the result of comparative experiments).

An experiment was conducted to determine the concentration of Percoll (Pharmacia, Product No. P1644) high density medium required to maintain unmodified Sephacryl S-300 (Pharmacia) solid phase support in suspension during assay.

A number of assay tubes were made up containing Sephacryl S-300 in 3% v/v Tween diluent (0.25 M TRIS buffer, pH 8.5 containing 0.1% w/v sodium azide 3% v/v Tween 20 (BDH Chemical Co. Limited)), separate tubes containing concentrations of commercial Percoll suspension ranging from 37-45% v/v, in 1% v/v steps. The contents of the tubes were shaken and the tubes left to stand in a test tube rack. After 4 hours the tubes were examined and it was found, in the tubes containing 39% v/v Percoll or less, that the Sephacryl had sedimented under the action of gravity. In the tubes containing 41% v/v Percoll or more, that the Sephacryl floated. The Sephacryl was maintained in suspension in the tube containing 40% Percoll.

These experiments indicated that a suitable concentration of Percoll for incubation of a mixture of Sephacryl S-300 in a typical assay liquid component is about 40% v/v.

EXAMPLE 2

A monoclonal/polyclonal antibody IRMA was investigated for the determination of alphfoetoprotein (AFP). The measurement of this protein in serum and amniotic fluid is used for detection of foetal abnormalities during pregnancy. The experiment was intended to show the differences between an assay conducted with agitation during incubation and without agitation (comparative examples). A binding assay of the invention was used to show the effect of density control during incubation.

Assay tubes were prepared in quadruplicate using standard solutions of AFP, of known concentration, ranging from 0 up to 600 $kU1^{-1}$ and assayed by IRMA procedures using in Example 2(a) (comparative example)—agitation without high density medium during incubation; in Example 2(b) (comparative example)—no agitation and no high density medium during incubation; and in Example 2 (c)—high density medium (HDM) and no agitation during incubation.

COMPARATIVE EXAMPLE 2(a)

Assay tubes were prepared in quadruplicate. 50 μl aliquots of each of an AFP standard, a tracer, and a solid phase reagent were pipetted into each assay tube in turn. The AFP standards consisted of solutions of AFP of known concentrations at 0 and in the range from 0.16 to 600 kU/1 in 50% bovine serum as diluent (0.25 M TRIS buffer, pH 8.5 containing 0.1% w/v sodium azide +50% bovine serum (Flow Laboratories, Flow Bovine Serum No. 29053104)). The tracer comprised $^{125}$I-labelled monoclonal anti-AFP, AFP 144 (V van Heyningen et al., Immunoassays for Clinical Chemistry, pages 509-515, published by Churchill Livingstone 1983), at a concentration of 400 ng/ml in 3% v/v sheep serum diluent (0.25 M TRIS buffer, pH 8.5, containing 0.1% w/v sodium azide +3% v/v sheep serum). The solid phase reagent comprised a suspension in 3% v/v Tween diluent (0.25 M TRIS buffer, pH 8.5, containing 0.1% w/v sodium azide +3% v/v Tween 20 (BDH Chemical Co. Limited)) of 12.5% v/v of a settled gel of unmodified Sephacryl S-300 (Pharmacia) having 8 mg/ml of goat anti-AFP gamma globulin (supplied by the Scottish Antibody Production Unit, Edinburgh) coupled to it.

After addition of the standard, tracer and solid phase reagents the contents of the assay tubes were mixed by vortex mixing, and the tubes were incubated at room temperature for 2 hours with constant agitation by means of an orbital shaker (150 revs/min, diameter of orbit 1 cm). At completion of the incubation, 1.5 ml of wash buffer (0.25 M TRIS buffer, pH 8.5 containing 0.1% w/v sodium azide +1% Bovine serum +1% Tween 20) was added to each tube.

The solid phase was then separated from the remainder of the incubation mixture using a separation method according to U.K. Pat. No. 1,566,098. 2 ml of a sucrose layering solution (10% w/v aqueous sucrose solution containing 0.1% w/v sodium azide and 1% v/v Tween 20) was added via a tubular metal probe to the base of the incubation mixture in each tube to form a discrete layer below the incubation mixture. The tubes were then left to stand at room temperature for 20 minutes, during which time the solid phase sedimented under the action of gravity from the incubation mixtures, through the sucrose layer, to the bases of the assay tubes. The liquid remainder of the incubation mixture and the upper part of the sucrose layer was removed from each tube by suction using a suction tube which was slowly lowered from the top into the assay tube, care being taken not to disturb the solid phase sediment. After suction, about 0.5 ml of the sucrose layer remained in the tubes containing all of the precipitated solid phase. A further 1.5 ml of wash buffer was then added to each tube and the sucrose separation procedure repeated, using a further 2 ml of sucrose layering solution. The radioactive counts bound by the solid phase in each tube were then counted using a gamma counter.

COMPARATIVE EXAMPLE 2(b)

The AFP IRMA procedure was repeated as described above except that agitation was omitted during incubation.

COMPARATIVE EXAMPLE 2(c)

The AFP IRMA procedure was repeated as described above, omitting agitation during incubation, except that Percoll, a high density medium, was incorporated in the incubate at a concentration just sufficient to keep the solid phase in suspension. Percoll (Product No.P1644, supplied by Sigma Chemical Company, St. Louis, U.S.A.) comprises a colloidal aqueous suspension of silica particles coated with non-dialysable polyvinylpyrrolidine of density 1.130±0.005 g/ml; conductivity 1.0 mS/cm; osmolality 20 mOs/kgH$_2$O; viscosity 10±5 cP at 20° C.; pH 8.9±0.3 at 20° C. and Refractive Index of 1.3540±0.0005 at 20° C. Commercial Percoll suspension was incorporated in the tracer and solid phase reagents used in this set of assays. The tracer contained 84% v/v and the solid phase 40% v/v Percoll, with the concentrations of the other constituents of these reagents suitably adjusted to give concentrations of these constituents in the final incubation mixture as for previous assays. The Percoll concentration in the solid phase reagent holds the solid phase in suspension, assisting in maintaining uniform composition of aliquots taken over an extended period of time. The concentrations of Percoll in the tracer and solid phase reagents gave a Percoll concentration of about 41.3% in the final incubation mixture being the concentration required to maintain the solid phase in suspension during incubation. Addition of 1.5 ml of wash buffer on completion of incubation diluted the Percoll permitting the Sephacryl S-300 solid phase to sediment under the action of gravity, during the sucrose layering separation.

The results obtained are given in FIG. 1 in the form of standard curves of the percentage of total counts bound (counts per minute) against AFP concentration (kU1$^{-1}$) in the standards used. Total counts were determined by measuring the counts given by a 50 μl aliquot of tracer alone. In FIG. 1, curve a) is the curve for the results obtained for the normal AFP IRMA, with agitation and without Percoll present during incubation; curve (b) is the curve obtained without agitation and without Percoll and curve (c) is the curve obtained for the modified assay which omitted agitation but included Percoll during incubation. Curves (a) and (c) give the results as the means of quadruplicate measurements. Curve (b) gives the results as the means of duplicate measurements. A comparison of curves (a) and (b) indicates the importance of agitation during incubation during a normal IRMA. Comparison of curves (a) and (c) indicates that the results obtained when Percoll is used and agitation is omitted are as good as, if not better than, the results obtained in a normal IRMA using agitation during incubation.

For determination of AFP in samples of unknown concentration a 50 μl aliquot of sample is used in place of the standard and the concentration of AFP determined by comparison of the result obtained with the appropriate standard curve.

EXAMPLE 3

A double monoclonal antibody IRMA was investigated for the determination of human Growth Hormone (hGH) in serum which employs a density separation of a granular particulate solid phase as described in British Patent specification No. 1,566,098. The assay involves a two hour inclusive incubation period including both labelled and solid phase monoclonal antibody together. Hence continuous agitation is required for this period in order to maintain the solid phase in suspension. The inclusion of a high density medium into the incubation mixture removes the need for agitation and does not affect the assay results. Two experiments were performed. In comparative Example 3(a) agitation was employed during incubation. In Example 3(b) no agitation was employed but the density of the assay mixture was closely controlled using an added high density medium.

COMPARATIVE EXAMPLE 3(a)

Thirty-eight patient samples were taken at random from a routine clinical laboratory intake and were assayed for hGH using the following protocol. Assay tubes were prepared in duplicate each pair of tubes containing either 50 Ml of patient sample or an hGH standard. (The standards used for establishing a standard curve were 0, 0.3125, 0.625, 1.25, 2.5, 5, 10, 20, 40, 80, 160, 320 and 640 mU hGH/l). The assay tubes each also contained 100 μl of $^{125}$I-labelled monoclonal antibody to hGH (ES3) at 40 ng/ml in diluent containing 1% v/v normal mouse serum, and 100 μl of a 10% (settled v/v) suspension of a monoclonal antibody to hGH immobilised on a solid phase (ES7-Sephacryl S-300) in diluent containing 2.5% v/v Tween 20. The monoclonal antibody-solid phase was prepared by coupling monoclonal antibody at 0.5 mg/ml to solid phase according to the standard procedure (Wright, J. F. and Hunter, W. M.) J. Immunol. Methods (1982) 48 pages 322-325). The diluent consisted of 0.1 M TRIS Hcl pH 8.0 and 2% v/v bovine serum. The contents of the assay tubes were mixed and agitated upon an orbital shaker (300 rpm; 2 cm orbit) for a period of 2 hours at room temperature, and then separated using two sucrose separations (see British Patent Specification No. 1,566,098). The radioactive counts bound by the separated solid phase in each assay tube were then counted.

COMPARATIVE EXAMPLE 3(b)

The protocol of Comparative Example 3(a) was followed except that 81% v/v Percoll was included in the $^{125}$I-labelled monoclonal antibody solution and 40.5% v/v Percoll was added to the suspension of immobilised monoclonal antibody. After mixing the resulting liquid mixture had a density approximately equal to the density of the monoclonal antibody-solid phase with the result that the solid phase remained in suspension during incubation at room temperature for two hours without agitation.

Figure 2:
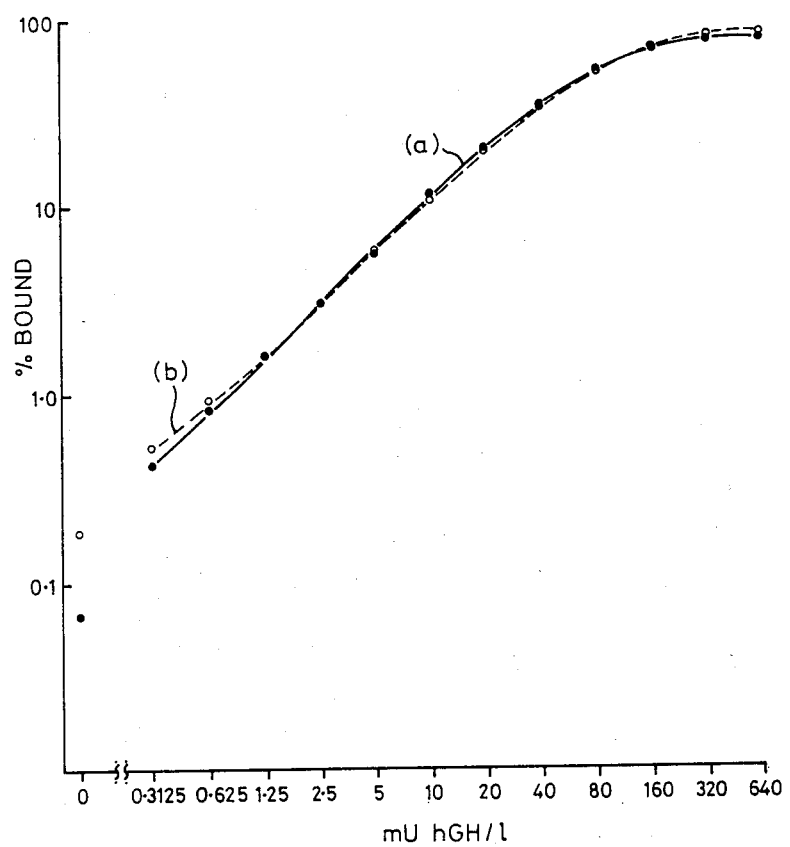
FIG. 2 shows standard curves for a double monoclonal antibody immunoradiometric assay for human growth hormone (curve (b) shows the result of an assay performed in accordance with the invention; curve (a) shows the result of a comparative experiment).

FIG. 2 shows the standard curves obtained using the protocol of comparative Example 3(a)—curve (a) and the protocol of Example 3(b)—curve (b). These results show little difference between the results despite the lack of agitation in the protocol of Example 3(b).

Figure 3:
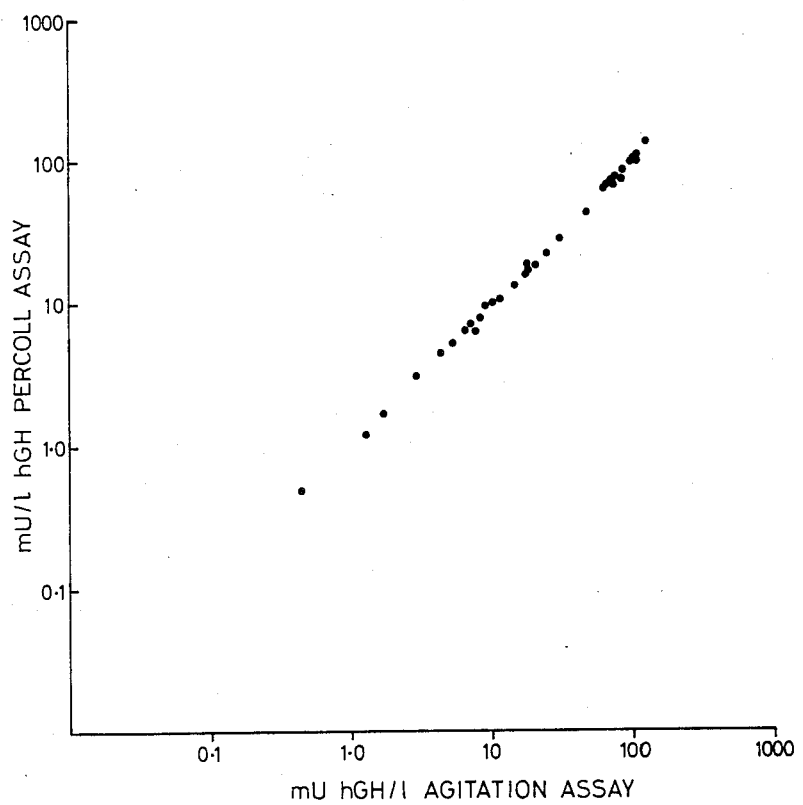
FIG. 3 shows a correlation plot of the results of an assay for human growth hormone performed in accordance with the invention (Y axis) and a comparative experiment (X axis), performed on clinical samples.

FIG. 3 shows a correlation plot of the results of the assay protocols of Comparative Example 3(a) and Example 3(b). The correlation coefficient is 0.997.

EXAMPLE 4

A double monoclonal antibody IRMA was investigated for the determination of thyroid stimulating hormone (TSH). The experiment was aimed at reducing the incubation time necessary for a successful assay result and at showing that density modification removes the need for agitation during incubation. This was achieved by replacing the solid phase monoclonal antibody with an antibody linked to avidin and a solid phase carrying biotin. In this way the formation of a ternary immunocomplex may occur in solution, the complex being subsequently removed by attachment to the solid phase through the biotin-avidin interaction.

COMPARATIVE EXAMPLE 4(a)

A standard curve was prepared for the TSH IRMA using the following protocol. Assay tubes were prepared containing a 100 μl each of a TSH standard in 35% v/v bovine serum in diluent (0, 0.156, 0.625, 2.5, 10, 40 and 160 mU TSH/l and 100 μl of $^{125}$I-labelled monoclonal antibody to TSH (323) at 20 ng/ml in diluent. The tubes were mixed and allowed to stand at room temperature for two hours. After this time period had elapsed 100 μl of a 10% (settled v/v) suspension of monoclonal antibody to TSH immobilised upon solid phase (42-Sephacryl S-300) in diluent containing 3% v/v Tween 20 was added. The diluent in each case consisted of 0.1 M TRIS HCl pH 8.0 and 2% v/v bovine serum. The tubes were then agitated for one hour on an orbital shaker (300 rpm; 1.3 cm orbit). The solid phase was then separated from the liquid component using two sucrose separations (see British Patent Specification No. 1,566,098). The radioactive counts bound by the separated solid phase in each assay tube were then counted.

EXAMPLE 4(b)

A standard curve was prepared for the TSH IRMA using the following protocol. Assay tubes were prepared containing TSH standard as for Comparative Example 4(a). To each assay tube was added 100 μl of $^{125}$I-labelled monoclonal antibody to TSH (323) at 20 ng/ml in diluent, plus monoclonal antibody to TSH (42) at 2000 ng/ml covalently attached to biotin and 60% Percoll (v/v) in diluent. The diluent was 0.1 M TRIS HCl pH 8.0 and 2% v/v bovine serum. The monoclonal antibody was attached to biotin by reacting 8.60 μg of monoclonal antibody in 1 ml of 0.1 M Bicine buffer at pH 7.5 with 90 μg of N-hydroxysuccinimidobiotin overnight at 4° C. After reaction, unreacted biotin was removed by an initial separation on a Pharmacia PD10 column in 0.25M TRIS HCl pH 8.5 and subsequently on a 20 cm Sephadex G50 SF column in 0.25M TRIS HCl, pH 8.5. The assay tubes were allowed to stand at room temperature for 2 hours 40 minutes. After this time period had elapsed, 100 μl of a 10% (settled v/v) suspension of avidin attached to a Sephacryl S-300 solid phase in diluent plus 3% (v/v) Tween 20 and 60% v/v Percoll was added to each tube. Avidin was attached to Sephacryl S-300 which had been oxidized with 5 mM periodate, at an initial concentration of 8 mg/ml in 0.1 M NaHCO$_3$ at pH 9.0 (Wright, J. F. and Hunter W. M., J. Immunol. Methods (1982) 48 pages 311-325). The tubes were allowed to stand for a further 20 minutes. The solid phase was then separated from the liquid component using two sucrose separations (see British Patent Specification No. 1,566,098). The radioactive counts bound by the separated solid phase in each assay tube were then measured.

Figure 4:
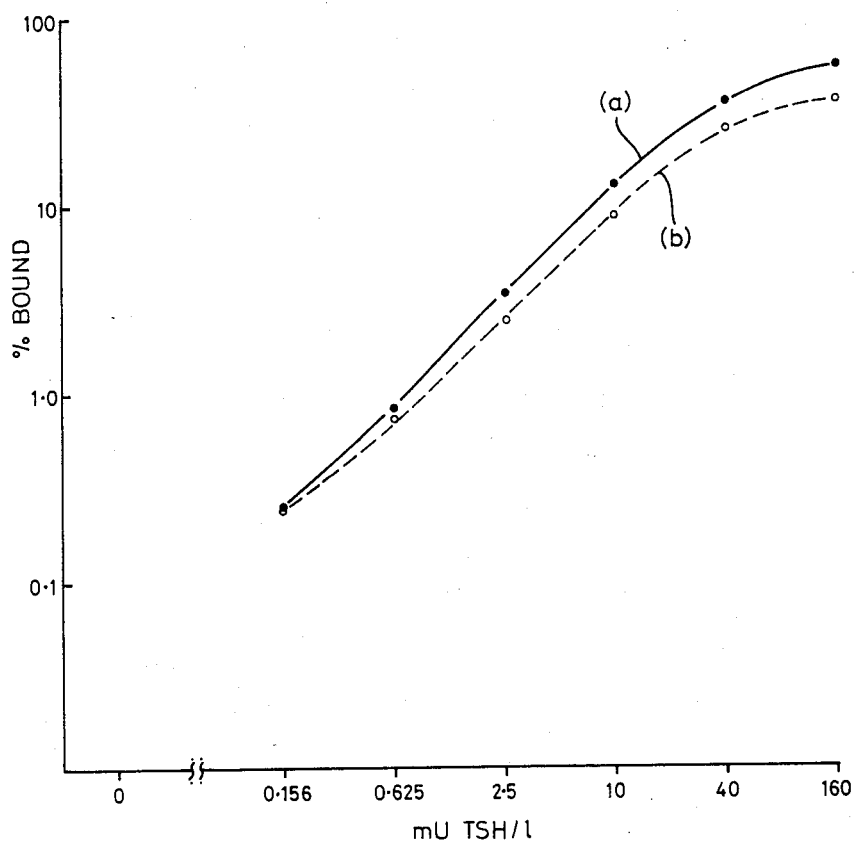
FIG. 4 shows standard curves for a double monoclonal antibody immunoradiometric assay for thyroid stimulating hormone; (curve (b) shows the result of an assay performed in accordance with the present invention; curve (a) is the result of a comparative experiment).

FIG. 4 shows the standard curve obtained using the protocol of Comparative Example 4(a)—curve (a) and Example 4(b)—curve (b). The results show that a reduction in the solid phase reaction time of an IRMA binding assay can be achieved using high avidity binding reagents such as avidin/biotin without a significant reduction in the sensitivity of the assay.

We claim:

1. In a heterogeneous binding assay in which a liquid component and a granular particulate solid phase are incubated together for a predetermined period of time, the improvement wherein the density of the liquid component is maintained substantially equal to the density of the granular particulate solid phase by the addition of a density modifying medium having a density greater than the density of the granular particulate solid phase and wherein the density of the liquid component is reduced upon expiry of the predetermined period of time to allow the granular particulate solid phase to separate under the influence of gravity by diluting the liquid component and density modifying medium mixture with a liquid of lower density than the mixture.

2. A heterogeneous binding assay according to claim 1 wherein the granular particulate solid phase comprises an allyl dextran, cross-linked with N,R'-methylene bisacrylamide and density modifying medium comprises a colloidal suspension of silica particles coated with polyvinylpyrrolidine.

3. A heterogenous binding assay according to claim 1 in which said liquid component is
   a solution containing components of the assay including a binding partner to which biotin is covalently attached and said particulate solid phase is a granular particulate solid phase to which avidin is covalently attached, the assay comprising the steps of:

incubating the solution components of the assay in the absence of the granular particulate solid phase, placing the incubated solution components and said density modifying medium in contact with the granular particulate solid phase thereby allowing association of avidin and biotin and, separating the granular particulate solid phase from the solution components.

4. A heterogeneous binding assay according to claim 1 which is an immunometric assay.

* * * * *

UNITED STATES PATENT AND TRADEMARK OFFICE
CERTIFICATE OF CORRECTION

PATENT NO. : 4,656,143

DATED : April 7, 1987

INVENTOR(S) : BAKER et al

It is certified that error appears in the above-identified patent and that said Letters Patent is hereby corrected as shown below:

On the cover page of the patent insert --[73] Assignee: BOOTS-CELLTECH DIAGNOSTICS LIMITED, Berkshire, England--.

Signed and Sealed this

Twenty-fifth Day of August, 1987

Attest:

DONALD J. QUIGG

Attesting Officer

Commissioner of Patents and Trademarks